US011964079B2

(12) United States Patent
Keshavarz-Nia et al.

(10) Patent No.: US 11,964,079 B2
(45) Date of Patent: Apr. 23, 2024

(54) INACTIVATION OF AEROSOLIZED MICROORGANISMS USING DIRECTED ENERGY

(71) Applicant: Raytheon Company, Waltham, MA (US)

(72) Inventors: Navid Keshavarz-Nia, Temecula, CA (US); David G. Manzi, Tucson, AZ (US); Ross E. Myrehn, Sr., Albuquerque, NM (US)

(73) Assignee: Raytheon Company, Tewksbury, MA (US)

( * ) Notice: Subject to any disclaimer, the term of this patent is extended or adjusted under 35 U.S.C. 154(b) by 376 days.

(21) Appl. No.: 17/208,038

(22) Filed: Mar. 22, 2021

(65) Prior Publication Data

US 2022/0047759 A1     Feb. 17, 2022

Related U.S. Application Data

(60) Provisional application No. 63/064,792, filed on Aug. 12, 2020.

(51) Int. Cl.
*A61L 9/18* (2006.01)
(52) U.S. Cl.
CPC ............ *A61L 9/18* (2013.01); *A61L 2209/111* (2013.01); *A61L 2209/16* (2013.01)
(58) Field of Classification Search
CPC ........................................................ A61L 9/18
USPC ........................................................ 422/21
See application file for complete search history.

(56) References Cited

U.S. PATENT DOCUMENTS

| 2009/0237067 | A1 | 9/2009 | Sun et al. |
| 2010/0113983 | A1 | 5/2010 | Heckerman et al. |
| 2011/0070624 | A1 | 3/2011 | Sun et al. |
| 2021/0299289 | A1* | 9/2021 | Raymond ................ A61L 2/12 |

OTHER PUBLICATIONS

Beggs, "The Airborne Transmission of Infection in Hospital Buildings: Fact or Fiction?", Indoor Built Environ., Nov. 2003, 10 pages.
Aliabadi et al., "Preventing Airborne Disease Transmission: Review of Methods for Ventilation Design in Health Care Facilities", Sage-Hindawi Access to Research Advances in Preventive Medicine, vol. 2011, Nov. 2011, 21 pages.
Tang et al., "Factors involved in the aerosol transmission of infection and control of ventilation in healthcare premises", Journal of Hospital Infection, Aug. 2006, 15 pages.

(Continued)

*Primary Examiner* — Kevin Joyner

(57) ABSTRACT

A system includes one or more radio frequency (RF) emitters configured to transmit RF energy into a specified area in order to inactivate one or more specified microorganisms in the specified area. The system also includes a control system configured to control the one or more RF emitters in order to adjust the RF energy transmitted by the one or more RF emitters. The control system is configured to obtain information identifying different types of microorganisms that are or might be present in the specified area over time and to adjust the RF energy transmitted by the one or more RF emitters in order to target the different types of microorganisms for inactivation over time.

20 Claims, 5 Drawing Sheets

(56) References Cited

OTHER PUBLICATIONS

Kowalski et al., "Airborne Respiratory Diseases and Mechanical Systems for Control of Microbes", HPAC Heating/ Piping/Air Conditioning, Jul. 1998, 11 pages.
Robach et al., "Ultrasonic absorption evidence for structural fluctuations in frog virus 3 and its subparticles", Proc. Natl. Acad. Sci. USA, vol. 80, Jul. 1983, 5 pages.
Cerf, "Absolute Measurement of Enhanced Fluctuations in Assemblies of Biomolecules by Ultrasonic Techniques", Biophys. J. Biophysical Society, vol. 47, Jun. 1985, 6 pages.
Dykeman et al., "Low Frequency Mechanical Modes of Viral Capsids: An Atomistic Approach", Physical Review Letters, Jan. 2008, 4 pages.
Balandin et al., "Vibrational Modes of Nano-Template Viruses", Journal of Biomedical Nanotechnology, vol. 1, No. 1, 2005, 6 pages.
Dykeman et al., "Atomistic modeling of the low-frequency mechanical modes and Raman spectra of icosahedral virus capsids", Physical Review, Feb. 2010, 14 pages.
Tsen et al., "Raman scattering studies of the low-frequency vibrational modes of bacteriophage M13 in water—observation of an axial torsion mode", Institute of Physics Publishing, Oct. 2006, 6 pages.
Liu et al., "Microwave resonant absorption of viruses through dipolar coupling with confined acoustic vibrations", Applied Physics Letters, Jan. 2009, 3 pages.
Bhardwaj et al., "Recent progress in nanomaterial-based sensing of airborne viral and bacterial pathogens", Environment International, Oct. 2020, 18 pages.
Schmittgen et al., "Quantitative Reverse Transcription-Polymerase Chain Reaction to Study mRNA Decay: Comparison of Endpoint and Real-Time Methods", Analytical Biochemistry, 2000, 11 pages.
IEEE, "IEEE Standard for Safety Levels with Respect to Human Exposure to Radio Frequency Electromagnetic Fields, 3 kHz to 300 GHz", IEEE Std. C95.1, 2005, 250 pages.
Wang et al., "Inactivation of Bacteriophage by Microwave Irradiation", Journal of Experimental Microbiology and Immunology, Dec. 2001, 10 pages.
Kakita et al., "Inactivation of Lactobacillus Bacteriophage PL-1 by Microwave Irradiation", Microbiol. Immunol., 1995, 6 pages.
Ellison et al., "Water: A dielectric reference", Journal of Molecular Liquids, Jan. 1996, 110 pages.
Yang et al., "Efficient Structure Resonance Energy Transfer from Microwaves to Confined Acoustic Vibrations in Viruses", Scientific Reports, Dec. 2015, 10 pages.
Fedorov, "Practical guidance on calculating resonant frequencies at four levels of diagnosis and inactivation of COVID-19 coronavirus", May 2020, 12 pages.
Heidelberg et al., "Effect of Aerosolization on Culturability and Viability of Gram-Negative Bacteria", Applied and Environmental Microbiology, Sep. 1997, 4 pages.
Goodlow et al., "Viability and Infectivity of Microorganisms in Experimental Airborne Infection", 1961, 6 pages.
Spena et al., "On the Optimal Indoor Air Conditions for SARS-COV-2 Inactivation. An Enthalpy-Based Approach", International Journal of Environmental Research and Public Health, Aug. 2020, 15 pages.
Chaterjee, "Virus and Vibrations I Adamas University", Mar. 2020, 3 pages.
"Transmission of SARS-COV-2: implications for infection prevention precautions", World Health Organization, Jul. 2020, 10 pages.
"Modes of transmission of virus causing COVID-19: implications for IPC precaution recommendations", World Health Organization, Mar. 2020, 3 pages.
Ford, "An Estimate of the Vibrational Frequencies of Spherical Virus Particles", Department of Physics and Astronomy Tufts University, Mar. 2003, 6 pages.
Wu et al., "In situ airborne virus inactivation by microwave irradiation", Chin. Sci. Bull., Mar. 2014, 8 pages.
Babincova et al., "Resonant absorption of ultrasound energy as a method of HIV destruction", Medical Hypotheses, Jun. 1999, 2 pages.
Pan et al., "Collection, particle sizing and detection of airborne viruses", Journal of Applied Microbiology, vol. 127, No. 6, Jun. 2019, 16 pages.
Al Ahmad et al., "Virus Detection by Monitoring Its Radio Frequency Response versus Temperature", 2016 Progress in Electromagnetic Research Symposium, Aug. 2016, 7 pages.
International Search Report dated Jul. 1, 2021 in connection with International Patent Application No. PCT/US2021/023997, 5 pages.
Written Opinion of the International Searching Authority dated Jul. 1, 2021 in connection with International Patent Application No. PCT/US2021/023997, 9 pages.

* cited by examiner

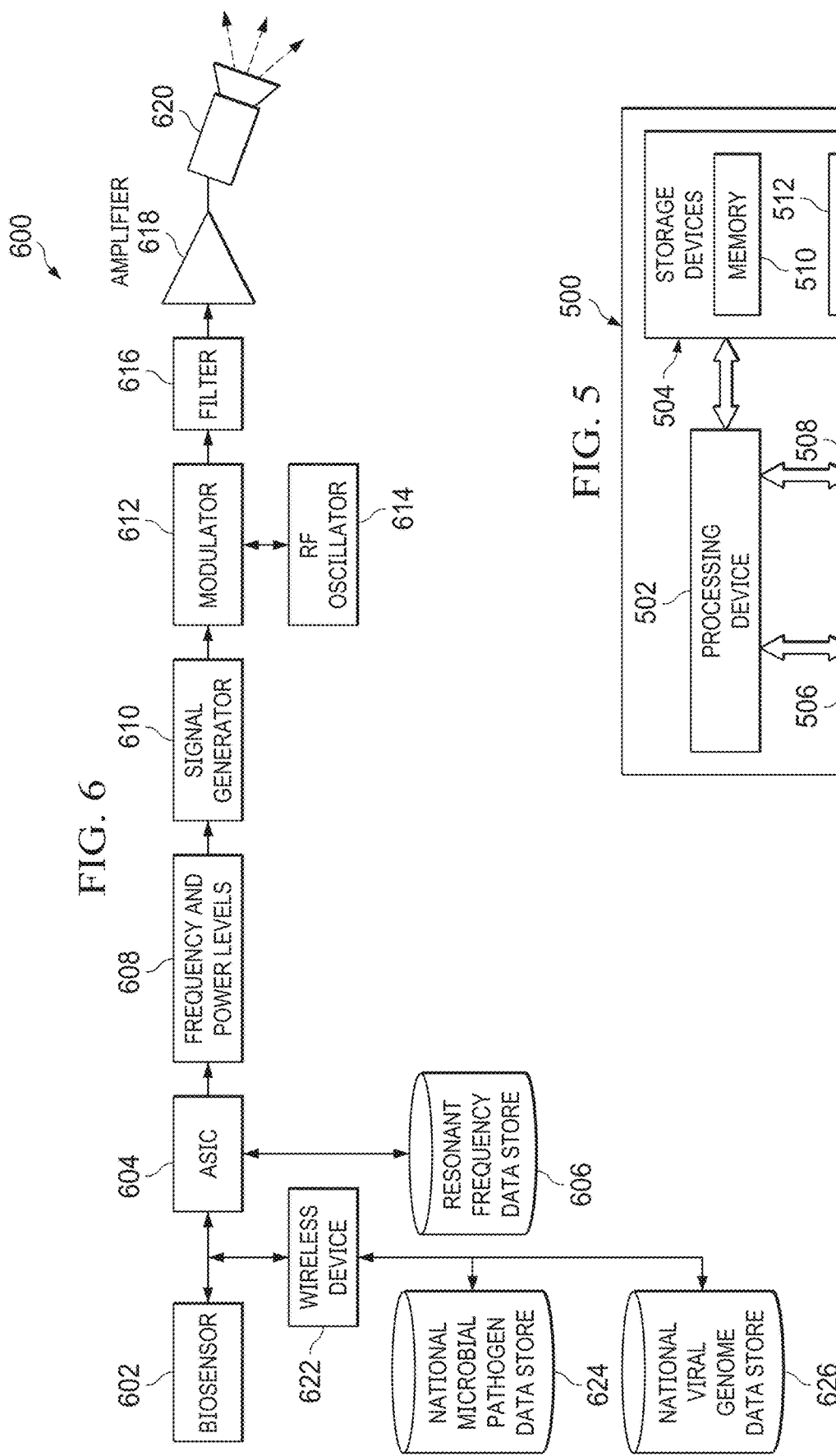

INACTIVATION OF AEROSOLIZED MICROORGANISMS USING DIRECTED ENERGY

CROSS-REFERENCE TO RELATED APPLICATION AND PRIORITY CLAIM

This application claims priority under 35 U.S.C. § 119(e) to U.S. Provisional Patent Application No. 63/064,792 filed on Aug. 12, 2020, which is hereby incorporated by reference in its entirety.

TECHNICAL FIELD

This disclosure relates generally to directed energy systems. More specifically, this disclosure relates to the inactivation of aerosolized microorganisms using directed energy.

BACKGROUND

The repercussions of airborne pathogens are well documented. In particular, exposure to infectious bio-aerosols results in the deposition of pathogens into the respiratory tracts of human hosts, causing disease and immunological response. As a consequence, airborne pathogens (such as COVID-19) result in immeasurable costs to public health, including death. This problem is prevalent in nearly any environment and poses significant danger in open areas, such as airports, malls, schools, and other places where large numbers of people congregate, and in places where heating, ventilation, and air conditioning (HVAC) systems routinely move air between locations.

SUMMARY

This disclosure relates to the inactivation of aerosolized microorganisms using directed energy.

In a first embodiment, a system includes one or more radio frequency (RF) emitters configured to transmit RF energy into a specified area in order to inactivate one or more specified microorganisms in the specified area. The system also includes a control system configured to control the one or more RF emitters in order to adjust the RF energy transmitted by the one or more RF emitters. The control system is configured to obtain information identifying different types of microorganisms that are or might be present in the specified area over time and to adjust the RF energy transmitted by the one or more RF emitters in order to target the different types of microorganisms for inactivation over time.

In a second embodiment, a method includes transmitting RF energy from one or more RF emitters into a specified area in order to inactivate one or more specified microorganisms in the specified area. The method also includes obtaining information identifying different types of microorganisms that are or might be present in the specified area over time. The method further includes controlling the one or more RF emitters in order to adjust the RF energy transmitted by the one or more RF emitters, where the RF energy transmitted by the one or more RF emitters is adjusted in order to target the different types of microorganisms for inactivation over time.

In a third embodiment, a non-transitory computer readable medium contains instructions that when executed cause at least one processor to initiate transmission of RF energy by one or more RF emitters into a specified area in order to inactivate one or more specified microorganisms in the specified area. The medium also contains instructions that when executed cause the at least one processor to obtain information identifying different types of microorganisms that are or might be present in the specified area over time. The medium further contains instructions that when executed cause the at least one processor to control the one or more RF emitters in order to adjust the RF energy transmitted by the one or more RF emitters. The RF energy transmitted by the one or more RF emitters is adjustable in order to target the different types of microorganisms for inactivation over time.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which:

FIG. 5 illustrates an example device or system supporting the inactivation of aerosolized microorganisms using directed energy according to this disclosure; and FIG. 6 illustrates a more specific example system for inactivating aerosolized microorganisms using directed energy according to this disclosure.

DETAILED DESCRIPTION

Figure 1:
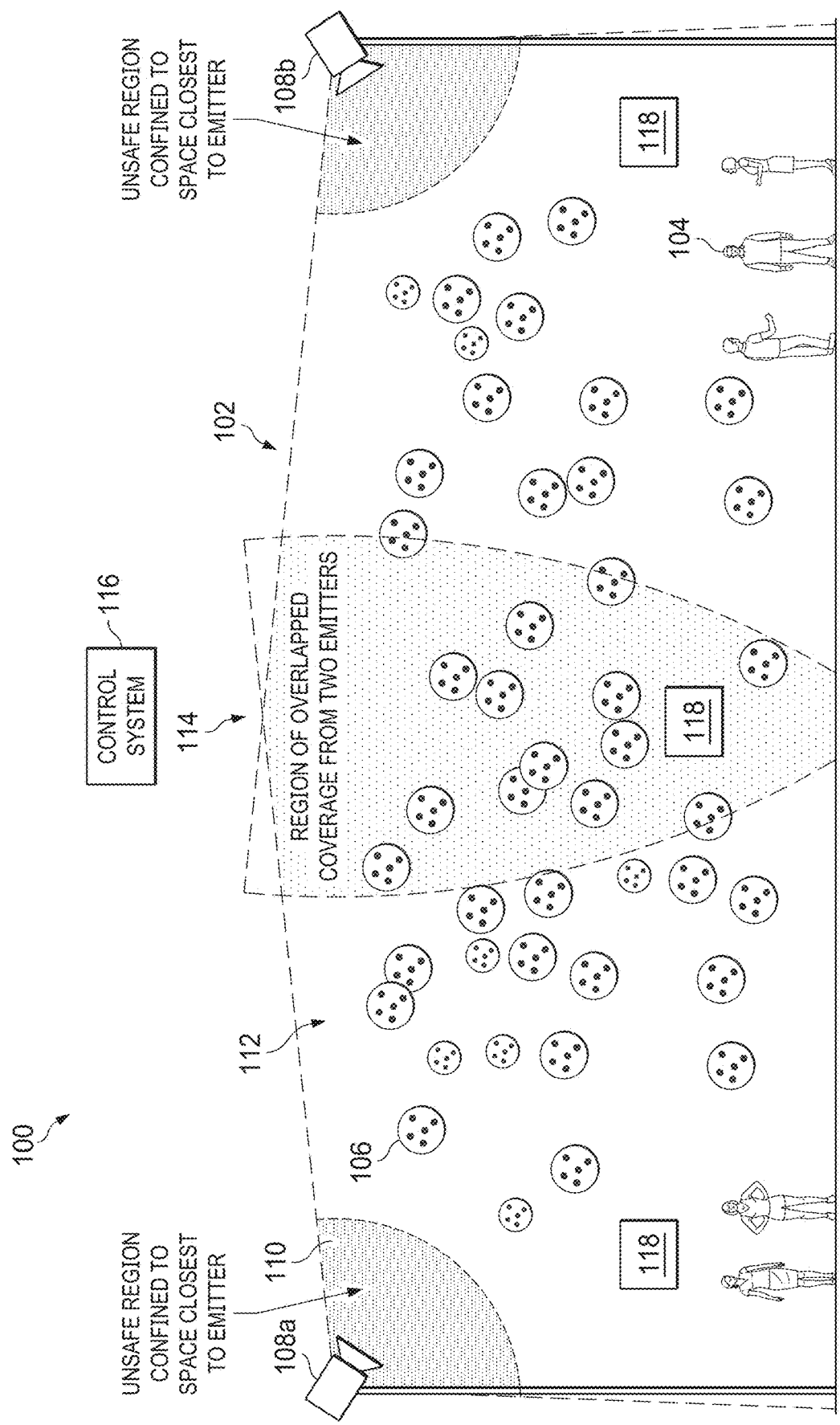
FIG. 1 illustrates an example system for inactivating aerosolized microorganisms using directed energy according to this disclosure.

FIGS. 1 through 6, described below, and the various embodiments used to describe the principles of the present disclosure are by way of illustration only and should not be construed in any way to limit the scope of this disclosure. Those skilled in the art will understand that the principles of the present disclosure may be implemented in any type of suitably arranged device or system.

As noted above, the repercussions of airborne pathogens are well documented. In particular, exposure to infectious bio-aerosols results in the deposition of pathogens into the respiratory tracts of human hosts, causing disease and immunological response. As a consequence, airborne pathogens (such as COVID-19) result in immeasurable costs to public health, including death. This problem is prevalent in nearly any environment and poses significant danger in open areas, such as airports, malls, schools, and other places where large numbers of people congregate, and in places where heating, ventilation, and air conditioning (HVAC) systems routinely move air between locations.

Several reports indicate that radio frequency (RF) energy can change, disrupt, or destroy viruses, possibly even COVID-19. Also, a recent study investigated the structure resonance energy transfer (SRET) from microwave signals to confined acoustic vibrations (CAVs) of the H3N2 virus in water-based solutions. However, to date, there is no evidence to suggest this phenomenon has been demonstrated for airborne COVID-19 or other pathogens in situ. Structure resonance energy transfer and other techniques have the potential to neutralize different pathogen target materials (including COVID-19) and change, disrupt, or destroy microorganisms without harming healthy material surrounding the target material.

This disclosure provides systems and methods for using structure resonance energy transfer or other techniques to inactivate microorganisms such as pathogens in situ. As described in more detail below, the systems and methods implement a solution to neutralize microorganisms such as airborne pathogens in situ by applying targeted microwave or other RF energy to damage the microorganisms' structures without harming the surrounding environment. Among other things, the systems and methods support features such as (i) inactivation of pathogens that occurs in airborne droplets using structure resonance energy transfer or other technique through the transmission of microwave or other RF energy, (ii) a self-adjusting solution that is software-controlled or otherwise controlled for pathogen inactivation based on environmental factors (like humidity, temperature, and pressure), and (iii) application of pulsed microwave or other RF energy to minimize power consumption and increase safety levels. Also, multi-pathogen neutralization can be achieved by modifying the resonant frequency, field strength, irradiation distance, and power level of the microwave or other RF energy using software or other automation, such as via artificial intelligence/machine learning (AI/ML). Overall, these systems and methods support the use of directed energy to inactive microorganisms, and this can be accomplished at RF field strength levels that satisfy IEEE or other safety standards.

There are various techniques that may be used to inactivate microorganisms using directed energy. For example, a resonance can be created between RF signals and acoustic modes within viral particles, which can induce fractures of the viral particles' capsid layers (this is also known as structure resonance energy transfer). As another example, dielectric heating of airborne water droplets by RF pulses can generate ultra/hyper-sonic signals within the water droplets, damaging the capsid layers of suspended viral particles. Similar techniques may be used with other microorganisms. Either approach has the potential for large area/volume deployment, depending on the overall coupling efficiencies, operating frequencies, and necessary power levels of the RF transmitters used. Note, however, that any other suitable mechanism for inactivating microorganisms using directed energy may be supported.

In some embodiments, since these approaches use directed energy to inactivate microorganisms like COVID-19, software/firmware or other controls can be used to adjust resonant frequency energy levels or other parameters to neutralize any number of microorganisms. For example, the directed energy can be customized to inactivate one or more specific types of pathogens being detected in a given area, and the specific types of pathogens being detected in that area can vary over time (so the directed energy can also vary over time). In this way, the systems and methods are adaptive and can respond to changes in the microorganisms being detected for a given area.

Specific implementations of these approaches can involve the use of a device or system that includes various components, such as a frequency generator, a transmitter, a power supply, and related elements. The device or system can also include a control unit (implemented in hardware or a combination of hardware and software/firmware) that is self-adjusting to modify transmission frequency, energy level, etc. needed to inactivate different microorganisms in situ. This provides a self-adjusting platform that applies energy to inactivate different airborne pathogens, including viruses or bacteria, or other microorganisms. This inactivation can be accomplished in real-time and without harm to the environment.

FIG. 1 illustrates an example system 100 for inactivating aerosolized microorganisms using directed energy according to this disclosure. As shown in FIG. 1, the system 100 is used with a specified area 102 that may be occupied by a number of people. The specified area 102 may represent an airport, mall, other business, religious building, or other location where a number of people 104 can congregate. The specified area 102 may also include varying amounts of airborne pathogens or other microorganisms 106, which are shown in exaggerated form in FIG. 1. In some cases, the microorganisms 106 may represent bacteria, viruses, or other pathogens contained in aerosolized or other airborne water droplets. In any adequately-large population, for example, it is common for at least some of the people 104 in the specified area 102 to be suffering from one or more types of respiratory illnesses, in which case the microorganisms 106 may include bacteria or viruses in airborne aerosolized droplets produced by coughing or sneezing. It is also possible for environmental factors to produce the microorganisms 106, such as when the microorganisms 106 include fungi spores.

The specified area 102 represents any suitable area in which microorganisms 106 may be inactivated as described below. In this example, the specified area 102 represents a large open area, but the size of the specified area 102 can vary in different applications. For example, in other instances, the specified area 102 may represent an area into which an HVAC system moves air from another location or from which the HVAC system moves air to another location, in which case the microorganisms 106 may originate in the specified area 102 or another area. The microorganisms 106 represent any of a number of pathogens that may cause illness in people 104 or other microorganisms, such as bacteria, viruses, or fungi.

In order to help inactivate the microorganisms 106, one or more RF emitters 108a-108b are positioned in or near the specified area 102. Each RF emitter 108a-108b is configured to generate microwave or other RF signals that can be used to inactivate the microorganisms 106 within the specified area 102 (meaning the microorganisms 106 are inactivate "in situ"). Each RF emitter 108a-108b includes any suitable structure configured to generate and transmit microwave or other RF signals. Each RF emitter 108a-108b can also be controllable so as to adjust the transmission or resonant frequency, power level/energy level/field strength, irradiation distance, or other parameters of the RF signals being generated. Among other things, this may allow the one or more RF emitters 108a-108b to generate microwave or other RF signals that are targeted at inactivating one or more specific types of microorganisms 106 and to change the microwave or other RF signals generated over time in order to inactivate different types of microorganisms 106 over time. Note that while two RF emitters 108a-108b are shown here, the number of RF emitters can vary based on a number of factors, such as the size of the specified area 102. Thus, the system may include a single RF emitter or more than two RF emitters. Also, each RF emitter 108a-108b may be located at any suitable position in or near the specified area 102.

As shown in FIG. 1, each RF emitter 108a-108b is associated with a near-field range 110 in which the emitted RF signals may have an unsafe field strength level (meaning the field strength may exceed an IEEE or other safety standard). At a farther distance from each RF emitter 108a-108b is a far-field range 112 in which the emitted RF signals may have a safe field strength level (meaning the field strength may not exceed an IEEE or other safety standard). Because of this, each RF emitter 108a-108b may be positioned so as to be spaced apart from the typical locations where people 104 may normally be found. This may be accomplished, for example, by mounting each RF emitter 108a-108b at a suitable distance above the ground or other location(s) where people 104 may normally be found. Depending on the arrangement of multiple RF emitters 108a-108b, there may be one or more regions 114 in which the far-field ranges 112 of two or more RF emitters 108a-108b overlap. In some cases, these regions 114 may represent areas in which the combined field strength from the two or more RF emitters 108a-108b is still within a safe level. This may be accomplished, for instance, by ensuring that the region 114 is located far enough from the RF emitters 108a-108b so that the collective field strength remains below an IEEE or other safety standard.

The exact characteristics of the RF energy generated by the RF emitters 108a-108b can vary based on a number of factors. For example, higher energy levels may be needed to inactivate one or more types of microorganisms 106 if the microorganisms 106 are farther from the RF emitters 108a-108b. This would expand the size of the near-field range 110, which may be accommodated by positioning the RF emitters 108a-108b at locations farther from where the people 104 are normally located. The energy levels may also vary depending on the specific type or types of microorganisms 106 to be inactivated, since some types of microorganisms 106 may be inactivated at lower energy levels compared to other types of microorganisms 106. As another example, the frequency of the RF energy may vary depending on the specific type or types of microorganisms 106 to be inactivated. For instance, different bacteria, viruses, and fungi spores typically require different resonant frequencies for damage to occur (assuming the mode of inactivation is structure resonance energy transfer). As still another example, the RF energy-to-sound energy conversion efficiency for the RF energy to the microorganisms 106 can vary based on environmental factors like air temperate, barometric pressure, and humidity.

For these and other reasons, a control system 116 may be used to control the operation of the RF emitters 108a-108b. For example, the control system 116 may receive inputs from various sensors, such as one or more sensors 118. The sensors 118 may include one or more biological sensors 118 configured to sense the various pathogens or other microorganisms 106 that are currently present in the specified area 102. The sensors 118 may also or alternatively include one or more environmental sensors configured to measure characteristics like air temperate, barometric pressure, and humidity. The sensors 118 may also or alternatively include one or more RF field strength sensors configured to measure the field strength of RF energy at one or more locations in the specified area 102. In general, any suitable type(s) of sensor(s) 118 may be used in the system 100, and each sensor 118 may be positioned in a suitable location based (among other things) on its intended function.

The control system 116 may use any suitable logic to control the operation of the RF emitters 108a-108b. For example, the control system 116 may receive measurement data from the sensors 118 and identify which pathogen(s) or other types of microorganisms 106 are most common, most dangerous, or should otherwise be targeted for inactivation, and the control system 116 can control the RF emitters 108a-108b to emit suitable RF energy in order to accomplish this. The control system 116 may also interact with an external source to identify one or more illnesses or other microorganisms 106 that might be present in the specified area 102 given recent local, national, or international trends, and the control system 116 may configure one or more sensors 118 to search for those specific types of microorganisms 106 (assuming the one or more sensors 118 can be reconfigured in this manner, which they may not be) or control the RF emitters 108a-108b to emit suitable RF energy in order to target those specific types of microorganisms 106. The control system 116 may further use environmental data to control the generation of RF energy by the RF emitters 108a-108b.

The control system 116 includes any suitable structure configured to control the operation of one or more RF emitters. For example, the control system 116 may include one or more computing devices, such as one or more desktop computers, laptop computers, or server computers. Note that while the control system 116 is shown here as being local to the specified area 102, at least part of the functionality of the control system 116 may be implemented elsewhere, such as in a remote server or computing cloud.

In some embodiments, the control system 116 uses artificial intelligence or other machine learning. For example, the control system 116 may identify how the measured levels of different types of microorganisms 106 change in response to different characteristics of the RF energy generated by the RF emitters 108a-108b, and the control system 116 may learn over time which RF energy characteristics (such as power levels, transmission or resonant frequencies, field strengths, and/or irradiation distances) are more effective at inactivating different types of microorganisms 106. The control system 116 may also consider and learn how different environmental or other factors affect the inactivation of the microorganisms 106. Example factors that may be considered and learned by the control system 116 include airflow distribution, ventilation system operation, air temperature, barometric pressure, air velocity, occupancy level, and relative humidity. Input from one or more RF field strength sensors 118 can be used by the control system 116 to help learn which RF energy characteristics do or do not cause the measured field strength to become too high (which is unsafe) or too low (which fails to provide adequate inactivation).

Note that it is also possible for this machine learning to occur in another device or system outside the system 100, such as when the control system 116 communicates with an external server, computing cloud, or other device or system that can process data from the control system 116. In some cases, this may allow machine learning to occur using data collected from multiple environments, such as data from multiple control systems 116 associated with multiple areas 102. As a particular example of this, the external device or system may be able to collect larger amounts of data from numerous control systems 116 and more effectively identify how specific microorganisms 106 can be targeted using RF energy.

Also note that the applied RF energy from the RF emitters 108a-108b typically needs to achieve a certain level of efficacy in order to successfully inactivate specific pathogens or other microorganisms 106 while remaining within IEEE or other safety standards. For example, the IEEE microwave safety standard requires that the spatial averaged value of power density in open public spaces not exceed the equivalent power density (P) of $100(f/3)^{1/5}$ W/m² at frequencies between 3 GHz and 96 GHz. The H3N2 virus is known to resonate at frequencies ranging between 8 GHz and 10 GHz, and recent findings show that COVID-19 has close structural similarities to the H3N2 virus. Thus, there is a good possibility that H3N2 and COVID-19 can achieve resonance at these frequencies if the correct field strength is obtained. The actual effectiveness of the applied RF energy can be confirmed in various ways, such as by using plaque assay, titer testing, or real-time reverse transcription polymerase chain reaction (RT-PCR) testing, to ensure inactivation of the microorganisms 106 in the specified area 102. Also, one or more RF field strength sensors 118 can be used to help measure the field strength to identify applied RF energy characteristics that result in acceptable (safe and effective) field strengths.

This approach therefore supports the inactivation of microorganisms 106 without negatively impacting the environment (such as humans, animals, and plants). This approach can be more effective in disinfecting the air as compared to other approaches, such as chemical processing, ultraviolet irradiation, ionization, acoustic/ultrasound treatment, laser usage, and heat processing. Moreover, this approach may avoid problems associated with other approaches, such as the avoidance of immunological responses like skin cancer.

Although FIG. 1 illustrates one example of a system 100 for inactivating aerosolized microorganisms using directed energy, various changes may be made to FIG. 1. For example, the system 100 may be associated with any number(s) and type(s) of area(s) 102, and each area 102 may have any suitable size, shape, and dimensions. Also, each area 102 may be associated with any number of RF emitters in any suitable arrangement. In addition, various components in FIG. 1 may be combined, further subdivided, replicated, omitted, or rearranged and additional components may be added according to particular needs.

Figure 2:
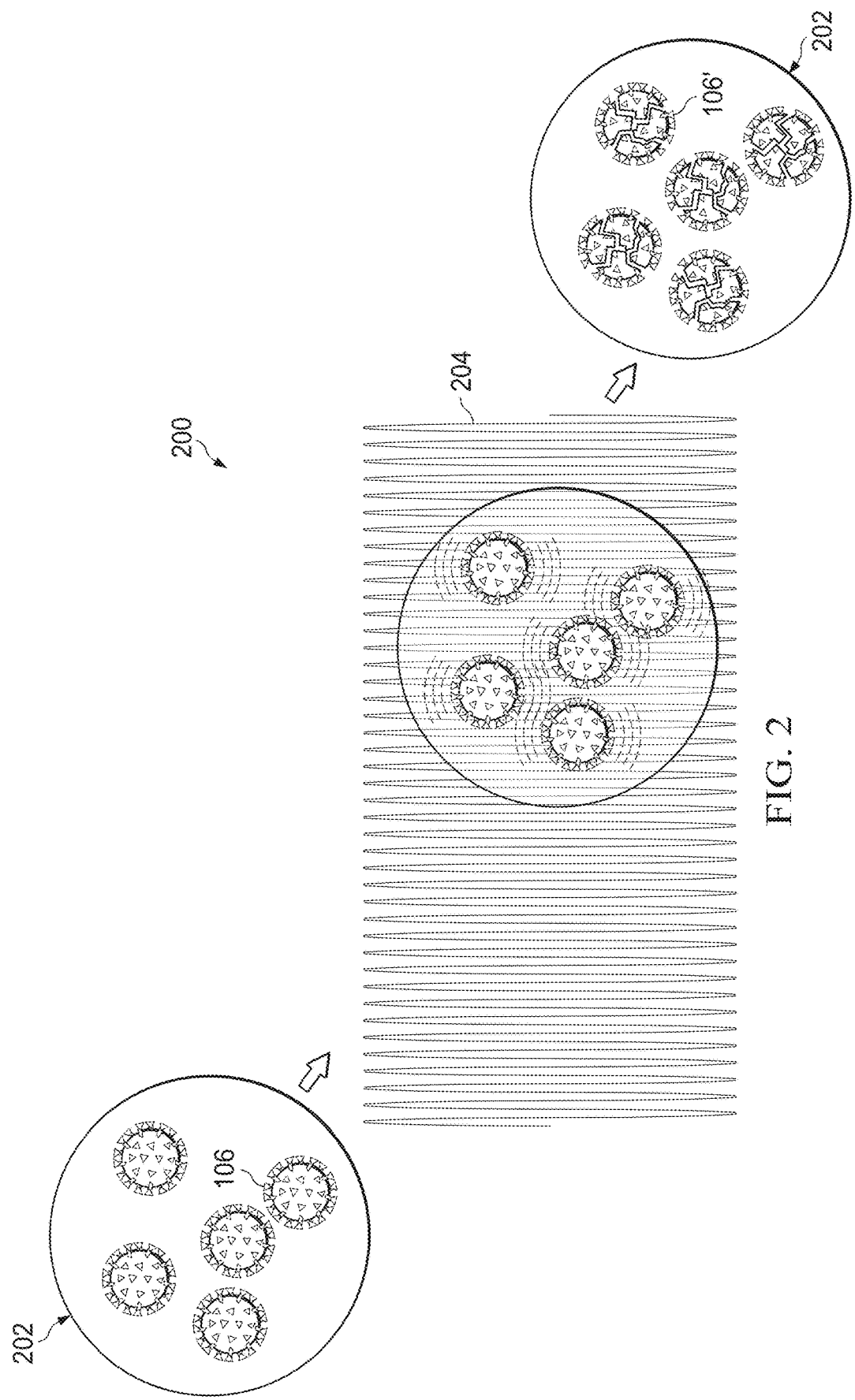
FIGS. 2 and 3 illustrate example mechanisms by which aerosolized microorganisms can be inactivated using directed energy according to this disclosure.
Figure 3:
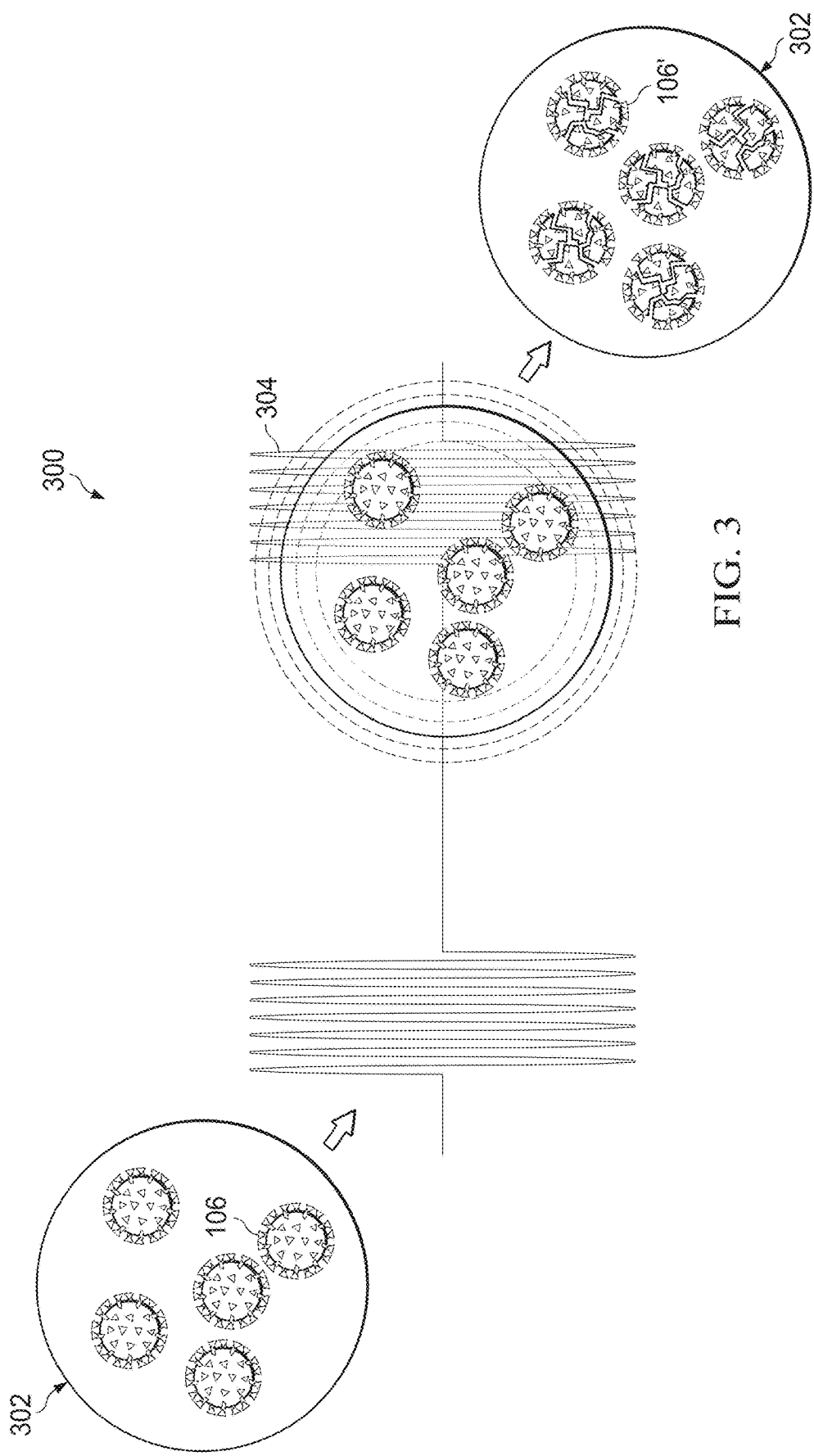

FIGS. 2 and 3 illustrate example mechanisms 200, 300 by which aerosolized microorganisms can be inactivated using directed energy according to this disclosure. As shown in FIG. 2, the mechanism 200 uses structure resonance energy transfer to inactivate microorganisms 106 contained in aerosolized or other airborne water droplets 202. As shown here, incident RF energy 204 from one or more RF emitters 108a-108b is applied to the water droplets 202. The incident RF energy 204 resonantly couples to acoustic modes in the microorganisms 106, such as via interactions with dipole moments in viral structures. This induces damaging vibrations to the microorganisms 106, such as to capsid shells of virus particles. This results in damaged and deactivated microorganisms 106' in the water droplets 202, which are generally unable to infect or otherwise negatively affect anyone. As a particular example of this, the vibrations can destroy the capsid shells of COVID-19 virus particles, which inactivates the viral particles since the viruses' RNA is no longer held within capsid shells that provide ACE-2 matching protein spikes.

As shown in FIG. 3, the mechanism 300 uses dielectric heating of aerosolized or other airborne water droplets 302 to inactivate microorganisms 106. As shown here, incident RF energy 304 from one or more RF emitters 108a-108b is pulsed, which repeatedly induces micro-degree heating of the water droplets 302. This heating creates pulsed volume changes in the water droplets 302, which result in ultra/hyper-sonic acoustic waves resonating within the water droplets 302. The acoustic waves damage the microorganisms 106, such as by damaging the capsid shells of virus particles. This results in damaged and deactivated microorganisms 106' in the water droplets 302, which are generally unable to infect or otherwise negatively affect anyone. Again, as a particular example of this, the acoustic waves can destroy the capsid shells of COVID-19 virus particles, which inactivates the viral particles since the viruses' RNA is no longer held within capsid shells that provide ACE-2 matching protein spikes.

Note that either mechanism 200 or 300 (or some other mechanism of inactivation) may be supported in the system 100. In some cases, the pulsed nature of the thermo-acoustic approach used in the mechanism 300 may prove to be efficacious at lower power levels, which may increase applicability and utility. However, this may not necessarily be the case in all instances, and either mechanism 200 or 300 or some other mechanism may be used by the system 100.

Although FIGS. 2 and 3 illustrate examples of mechanisms 200, 300 by which aerosolized microorganisms can be inactivated using directed energy, various changes may be made to FIGS. 2 and 3. For example, an environment may include any number of water droplets or other aerosolized/airborne droplets each with any number of microorganisms 106. Also, the described mechanisms 200, 300 may be used to inactivate microorganisms 106 that are located on the surfaces of objects in a specified area 102.

Figure 4:
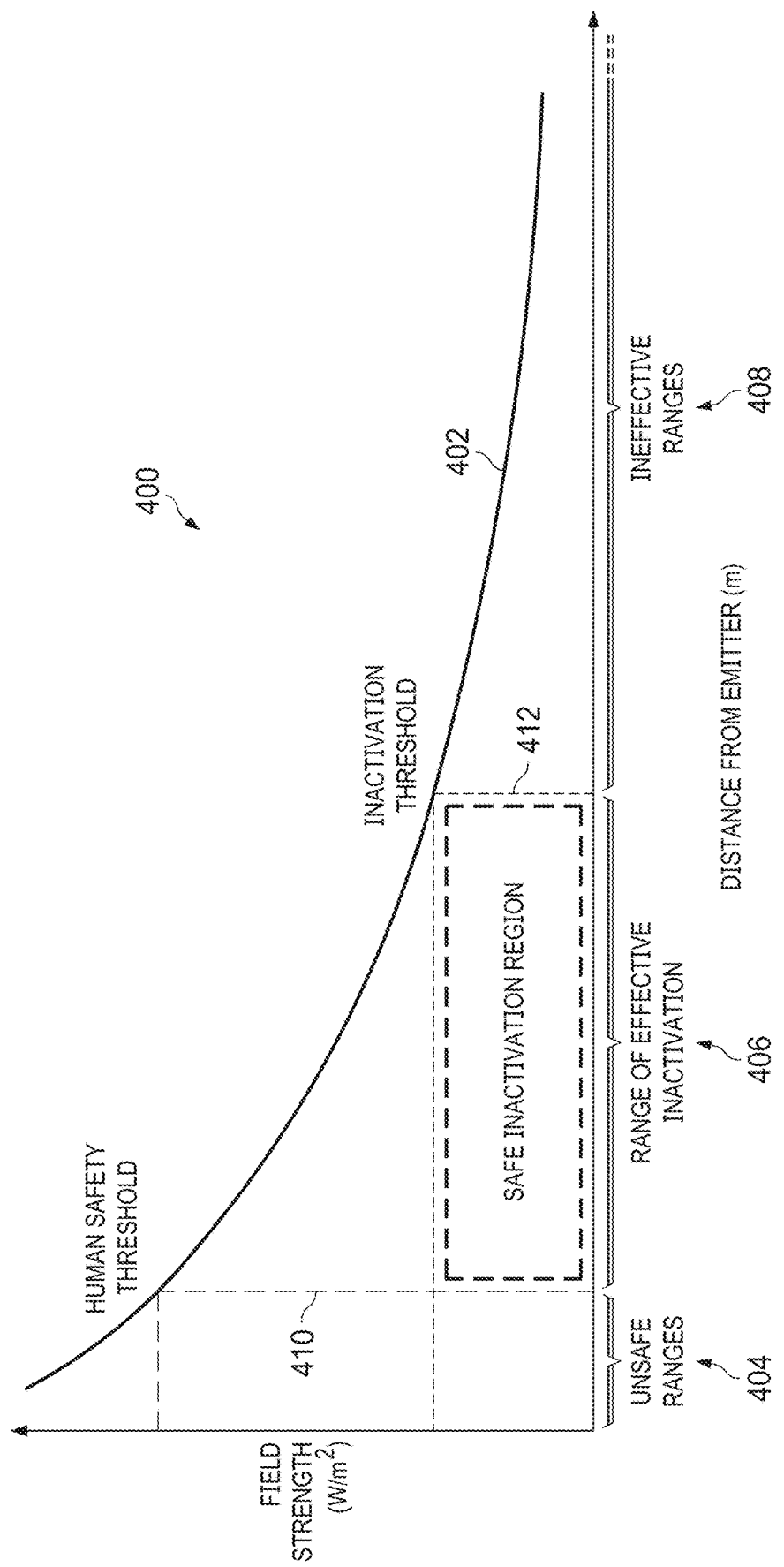
FIG. 4 illustrates an example graph showing field strengths for directed energy used to inactivate aerosolized microorganisms according to this disclosure.

FIG. 4 illustrates an example graph 400 showing field strengths for directed energy used to inactivate aerosolized microorganisms according to this disclosure. In particular, the graph 400 includes a line 402 that indicates how the field strength of an RF emitter 108a-108b can vary with distance from the RF emitter 108a-108b.

As can be seen in FIG. 4, the distance from the RF emitter 108a-108b is divided into three ranges, namely an unsafe range 404, an effective inactivation range 406, and an ineffective inactivation range 408. The unsafe range 404 includes the distances from the RF emitter 108a-108b at which the RF field strength is unsafe or above an IEEE or other safety standard threshold 410. The effective inactivation range 406 includes the distances from the RF emitter 108a-108b at which the RF field strength is (i) safe or below the threshold 410 and (ii) effective at inactivating a specific microorganism 106 because the field strength remains above an inactivation threshold 412. The ineffective inactivation range 408 includes the distances from the RF emitter 108a-108b at which the RF field strength is (i) safe or below the threshold 410 but (ii) ineffective at inactivating the specific microorganism 106 because the field strength is below the inactivation threshold 412.

Note that the graph 400 can vary based on a number of factors, such as (i) the specific RF emitter 108a-108b being used and (ii) the specific microorganism 106 being inactivated. For example, the specific RF emitter 108a-108b being used may have different or adjustable power levels that can alter the field strength being produced, so the line 402 can vary based on the actual power level in use (which can affect the size of the ranges 404, 406, 408). As another example, the specific microorganism 106 to be inactivated may have its own unique inactivation threshold 412. Also note that the information contained in the graph 400 (and similar graphs) may be used in any suitable manner. For instance, the control system 116 may use the information contained in the graph 400 to identify a desired transmit power for the RF emitter 108a-108b given a specific microorganism 106 to be inactivated, and the specific transmit power can be selected to be within the range 406 (and possibly learned using AI/ML or otherwise established).

Although FIG. 4 illustrates one example of a graph 400 showing field strengths for directed energy used to inactivate aerosolized microorganisms, various changes may be made to FIG. 4. For example, the graph 400 can vary as described above, and the specific graph 400 shown in FIG. 4 is for illustration and explanation only.

FIG. 5 illustrates an example device or system 500 supporting the inactivation of aerosolized microorganisms using directed energy according to this disclosure. In some embodiments, one or more functions related to the approaches described above (such as the control and self-adaptive functionality of the system 100) are performed using the device or system 500. The device or system 500 may, for example, be used to implement at least part of the control system 116.

As shown in FIG. 5, the device or system 500 may include at least one processing device 502, at least one storage device 504, at least one communications unit 506, and at least one input/output (I/O) unit 508. The processing device 502 may execute instructions that can be loaded into a memory 510. The processing device 502 includes any suitable number(s) and type(s) of processors or other processing devices in any suitable arrangement. Example types of processing devices 502 include one or more microprocessors, microcontrollers, digital signal processors (DSPs), application specific integrated circuits (ASICs), field programmable gate arrays (FPGAs), or discrete circuitry.

The memory 510 and a persistent storage 512 are examples of storage devices 504, which represent any structure(s) capable of storing and facilitating retrieval of information (such as data, program code, and/or other suitable information on a temporary or permanent basis). The memory 510 may represent a random access memory or any other suitable volatile or non-volatile storage device(s). The persistent storage 512 may contain one or more components or devices supporting longer-term storage of data, such as a read only memory, hard drive, Flash memory, or optical disc.

The communications unit 506 supports communications with other systems or devices. The communications unit 206 may support communications through any suitable physical or wireless communication link(s), such as a network or dedicated connection(s). As a particular example, the communications unit 506 may support communication with the RF emitters 108a-108b (used to transmit and receive RF signals) or sensors 118 (used to measure humidity, temperature, pressure, or other characteristics in an environment).

The I/O unit 508 allows for input and output of data. For example, the I/O unit 508 may provide a connection for user input through a keyboard, mouse, keypad, touchscreen, or other suitable input device. The I/O unit 508 may also send output to a display or other suitable output device. Note, however, that the I/O unit 508 may be omitted if the device or system 500 does not require local I/O, such as when the device or system 500 represents a server or other component that can be accessed remotely over a network.

Although FIG. 5 illustrates one example of a device or system 500 supporting the inactivation of aerosolized microorganisms using directed energy, various changes may be made to FIG. 5. For example, computing devices and systems come in a wide variety of configurations, and FIG. 5 does not limit this disclosure to any particular device or system. Also, various components in FIG. 5 may be combined, further subdivided, replicated, omitted, or rearranged and additional components may be added according to particular needs.

FIG. 6 illustrates a more specific example system 600 for inactivating aerosolized microorganisms using directed energy according to this disclosure. The system 600 may, for example, represent one specific implementation of the system 100. As shown in FIG. 6, the system 600 includes one or more biosensors 602, which may represent one or more sensors 118 that are designed to detect one or more specific types of microorganisms 106. For example, the one or more biosensors 602 may represent wireless or other sensors that collect samples of air for sensing of one or more specific types of microorganisms 106 in the sampled air.

Measurements from the one or more biosensors 602 are provided to an ASIC or other processor 604, which may represent at least a portion of the control system 116. In this example, the ASIC or other processor 604 may receive bio-data from the one or more biosensors 602 and compare it against information in a pathogen data store 606, which can be used to store information associated with known microorganisms 106 and provide information about inactivating those microorganisms 106 (such as by identifying their resonant frequencies and associated emitter power levels). The ASIC or other processor 604 can retrieve specific information 608 for one or more detected types of microorganisms 106 and forward the information 608 to a signal generator 610. The signal generator 610 uses the information 608 to generate a signal having a suitable waveform, such as a continuous-wave or pulsed waveform. A modulator 612 modulates the signal from the signal generator 610 using an appropriate RF oscillator 614 (which may be selected based on the desired frequency and power level). The resulting signal is filtered using a filter 616 and amplified using a power amplifier 618. The amplified signal is transmitted via one or more antennas 620 in order to inactivate the detected type(s) of microorganisms 106. The components 604, 606, 610-620 may, for example, represent at least part of one or more RF emitters 108a-108b.

In this example, a wireless or other device 622 can collect information about pathogens or other microorganisms 106 from one or more external sources and provide that information to the ASIC or other processor 604 and/or the one or more biosensors 602. For example, the device 622 may obtain information from a national or other microbial pathogen data store 624, a national or other viral genome data store 626, or other suitable external source of information. This type of information may be useful in identifying likely pathogens or other microorganisms 106 currently being sensed in the system 600.

Although FIG. 6 illustrates one more specific example of a system 600 for inactivating aerosolized microorganisms using directed energy, various changes may be made to FIG. 6. For example, various components in FIG. 6 may be combined, further subdivided, replicated, omitted, or rearranged and additional components may be added according to particular needs.

In some embodiments, various functions described in this patent document are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive (HDD), a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable storage device.

It may be advantageous to set forth definitions of certain words and phrases used throughout this patent document. The terms "application" and "program" refer to one or more computer programs, software components, sets of instructions, procedures, functions, objects, classes, instances, related data, or a portion thereof adapted for implementation in a suitable computer code (including source code, object code, or executable code). The term "communicate," as well as derivatives thereof, encompasses both direct and indirect communication. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

The description in the present disclosure should not be read as implying that any particular element, step, or function is an essential or critical element that must be included in the claim scope. The scope of patented subject matter is defined only by the allowed claims. Moreover, none of the claims invokes 35 U.S.C. § 112(f) with respect to any of the appended claims or claim elements unless the exact words "means for" or "step for" are explicitly used in the particular claim, followed by a participle phrase identifying a function. Use of terms such as (but not limited to) "mechanism," "module," "device," "unit," "component," "element," "member," "apparatus," "machine," "system," "processor," or "controller" within a claim is understood and intended to refer to structures known to those skilled in the relevant art, as further modified or enhanced by the features of the claims themselves, and is not intended to invoke 35 U.S.C. § 112(f).

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure.

What is claimed is:

1. A system comprising:
   multiple radio frequency (RF) emitters configured to transmit RF energy into a specified area in order to inactivate one or more specified microorganisms in the specified area; and
   a control system configured to control the RF emitters in order to adjust the RF energy transmitted by the RF emitters, wherein the control system is configured to:
   obtain information identifying different types of microorganisms that are or might be present in the specified area over timed;
   adjust the RF energy transmitted by the RF emitters in order to target the different types of microorganisms for inactivation over time; and
   maintain a collective field strength below a safety standard threshold within an overlapping region of at least two of the RF emitters when inactivation of a specified microorganism requires increasing the RF energy of the RF emitters.

2. The system of claim 1, wherein the control system is configured to use machine learning to identify one or more characteristics of the RF energy to be used in order to target the different types of microorganisms for inactivation.

3. The system of claim 2, wherein the one or more characteristics of the RF energy comprise at least one of: a transmission frequency of the RF energy, a power or an energy level of the RF energy, a field strength of the RF energy, and an irradiation distance of the RF energy.

4. The system of claim 1, wherein:
   the system further comprises one or more sensors configured to identify the different types of microorganisms in the specified area; and
   the control system is configured to adjust the RF energy based on the different types of microorganisms identified in the specified area.

5. The system of claim 1, wherein the control system is configured to obtain information from one or more external sources identifying likely types of microorganisms that might be sensed in the specified area.

6. The system of claim 1, wherein:
   the system further comprises one or more sensors configured to identify at least one of: one or more environmental characteristics in the specified area and one or more RF field strengths in the specified area; and
   the control system is configured to adjust the RF energy based on at least one of: the one or more environmental characteristics and the one or more RF field strengths.

7. The system of claim 1, wherein the RF emitters are positioned such that any portion of the specified area in which the RF energy emitted by the RF emitters overlaps has the collective field strength below the safety standard threshold.

8. A method comprising:
   transmitting RF energy from multiple radio frequency (RF) emitters into a specified area in order to inactivate one or more specified microorganisms in the specified area;
   obtaining information identifying different types of microorganisms that are or might be present in the specified area over time;
   controlling the RF emitters in order to adjust the RF energy transmitted by the RF emitters;
   adjusting the RF energy transmitted by the RF emitters in order to target the different types of microorganisms for inactivation over time; and
   maintaining a collective field strength below a safety standard threshold within an overlapping region of at least two of the RF emitters when inactivation of a specified microorganism requires increasing the RF energy of the RF emitters.

9. The method of claim 8, further comprising:
   using machine learning to identify one or more characteristics of the RF energy to be used in order to target the different types of microorganisms for inactivation.

10. The method of claim 9, wherein the one or more characteristics of the RF energy comprise at least one of: a transmission frequency of the RF energy, a power or an energy level of the RF energy, a field strength of the RF energy, and an irradiation distance of the RF energy.

11. The method of claim 8, wherein:
    the method further comprises identifying the different types of microorganisms in the specified area using one or more sensors; and the RF energy is adjusted based on the different types of microorganisms identified in the specified area by the one or more sensors.

12. The method of claim 8, further comprising:
obtaining information from one or more external sources identifying likely types of microorganisms that might be sensed in the specified area.

13. The method of claim 8, wherein:

the method further comprises identifying at least one of: one or more environmental characteristics in the specified area and one or more RF field strengths in the specified area; and the RF energy is adjusted based on at least one of: the one or more environmental characteristics and the one or more RF field strengths.

14. The method of claim 8, wherein the RF energy transmitted by the RF emitters is adjusted in order to inactivate the one or more specified microorganisms in the specified area via at least one of:

structure resonance energy transfer; and dielectric heating of airborne water droplets.

15. A non-transitory computer readable medium containing instructions that when executed cause at least one processor to:

initiate transmission of radio frequency (RF) energy by multiple RF emitters into a specified area in order to inactivate one or more specified microorganisms in the specified area;

obtain information identifying different types of microorganisms that are or might be present in the specified area over time;

control the RF emitters in order to adjust the RF energy transmitted by the RF emitters;

adjust the RF energy transmitted by the RF emitters in order to target the different types of microorganisms for inactivation over time; and maintain a collective field strength below a safety standard threshold within an overlapping region of at least two of the RF emitters when inactivation of a specified microorganism requires increasing the RF energy of the RF emitters.

16. The non-transitory computer readable medium of claim 15, further containing instructions that when executed cause the at least one processor to use machine learning to identify one or more characteristics of the RF energy to be used in order to target the different types of microorganisms for inactivation.

17. The non-transitory computer readable medium of claim 16, wherein the one or more characteristics of the RF energy comprise at least one of: a transmission frequency of the RF energy, a power or an energy level of the RF energy, a field strength of the RF energy, and an irradiation distance of the RF energy.

18. The non-transitory computer readable medium of claim 15, further containing instructions that when executed cause the at least one processor to obtain information identifying the different types of microorganisms in the specified area from one or more sensors;

wherein the instructions that when executed cause the at least one processor to control the RF emitters in order to adjust the RF energy comprise instructions that when executed cause the at least one processor to adjust the RF energy based on the different types of microorganisms identified in the specified area.

19. The non-transitory computer readable medium of claim 15, further containing instructions that when executed cause the at least one processor to obtain information from one or more external sources identifying likely types of microorganisms that might be sensed in the specified area.

20. The non-transitory computer readable medium of claim 15, further containing instructions that when executed cause the at least one processor to obtain information identifying at least one of: one or more environmental characteristics in the specified area and one or more RF field strengths in the specified area;

wherein the instructions that when executed cause the at least one processor to control the RF emitters in order to adjust the RF energy comprise instructions that when executed cause the at least one processor to adjust the RF energy based on at least one of: the one or more environmental characteristics and the one or more RF field strengths.

* * * * *